US010578422B2

(12) United States Patent
Yamada et al.

(10) Patent No.: US 10,578,422 B2
(45) Date of Patent: Mar. 3, 2020

(54) DEVICES, SYSTEMS, METHODS AND STORAGE MEDIUMS USING FULL RANGE OPTICAL COHERENCE TOMOGRAPHY

(71) Applicants: Canon U.S.A. Inc., Melville, NY (US); The General Hospital Corporation, Boston, MA (US)

(72) Inventors: Daisuke Yamada, Cambridge, MA (US); Guillermo J Tearney, Cambridge, MA (US)

(73) Assignees: Canon U.S.A., Inc., Melville, NY (US); The General Hospital Corporation, Boston, MA (US)

( * ) Notice: Subject to any disclaimer, the term of this patent is extended or adjusted under 35 U.S.C. 154(b) by 316 days.

(21) Appl. No.: 15/617,928

(22) Filed: Jun. 8, 2017

(65) Prior Publication Data

US 2018/0003481 A1 Jan. 4, 2018

Related U.S. Application Data

(60) Provisional application No. 62/347,246, filed on Jun. 8, 2016.

(51) Int. Cl.
*G01B 9/02* (2006.01)
*A61B 5/00* (2006.01)

(52) U.S. Cl.
CPC ........ *G01B 9/02091* (2013.01); *A61B 5/0033* (2013.01); *A61B 5/0066* (2013.01);
(Continued)

(58) Field of Classification Search
CPC ... A61B 5/0066; A61B 5/0033; A61B 5/0073; G01B 9/02091; G01B 9/02004; G01B 9/0205

See application file for complete search history.

(56) References Cited

U.S. PATENT DOCUMENTS 5,795,295 A * 8/1998 Hellmuth ............. A61B 5/0059
250/201.3
7,366,376 B2  4/2008 Shishkov et al.
(Continued)

FOREIGN PATENT DOCUMENTS

CN        202096197 U    1/2012
WO     2015121853 A1    8/2015
(Continued)

OTHER PUBLICATIONS

Beaudette, K. et al., "Towards in vivo laser coagulation and concurrent optical coherence tomography through double-clad fiber devices", Proc. SPIE, Multimodal Biomedical Imaging XI, Mar. 7, 2016, vol. 9701 (English abstract).
(Continued)

*Primary Examiner* — Jonathan M Hansen
(74) *Attorney, Agent, or Firm* — Canon U.S.A., Inc. I.P. Division

(57) ABSTRACT

One or more devices, systems, methods and storage mediums for performing continuously, full range optical coherence tomography (OCT) without losing A-lines are provided. Examples of such applications include imaging, evaluating and diagnosing biological objects, such as, but not limited to, for cardio and/or ophthalmic applications, and being obtained via one or more optical instruments, such as, but not limited to, optical probes (e.g., common path probes), catheters, endoscopes, phase shift units (e.g., galvanometer scanner) and bench top systems. Preferably, the OCT devices, systems methods and storage mediums include or involve a phase shift device including at least a galvanometer scanner. The galvanometer scanner is preferably applied with or to a voltage with a triangle shape, the voltage having continuity or absolute constant frequency to obtain continuous images without losing any A-lines. The method(s) may include background subtraction, image shift-
(Continued)

ing to compensate phase shifts and a DC noise reduction algorism.

23 Claims, 13 Drawing Sheets

(52) U.S. Cl.
CPC .......... *A61B 5/0073* (2013.01); *A61B 5/6852* (2013.01); *G01B 9/02002* (2013.01); *G01B 9/0205* (2013.01); *G01B 9/02044* (2013.01); *G01B 9/02051* (2013.01); *G01B 9/02089* (2013.01)

(56) References Cited

U.S. PATENT DOCUMENTS

| | | | |
|---|---|---|---|
| 7,710,577 B2 | 5/2010 | Yatagai et al. | |
| 7,728,985 B2 | 6/2010 | Feldchtein et al. | |
| 7,843,572 B2 | 11/2010 | Tearney et al. | |
| 7,929,146 B2 | 4/2011 | Izatt et al. | |
| 8,115,934 B2 | 2/2012 | Boppart et al. | |
| 8,180,134 B2 | 5/2012 | Wang | |
| RE43,875 E | 12/2012 | Shishkov et al. | |
| 8,363,225 B2 | 1/2013 | Rolland et al. | |
| 8,605,287 B2 | 12/2013 | Ko et al. | |
| 8,619,184 B2 | 12/2013 | Podoleanu | |
| RE45,142 E | 9/2014 | Kehrer et al. | |
| 8,842,288 B2 | 9/2014 | Ogawa | |
| 8,928,889 B2 | 1/2015 | Tearney et al. | |
| 9,087,368 B2 | 7/2015 | Tearney et al. | |
| 9,095,281 B2 | 8/2015 | Sharma et al. | |
| 9,332,942 B2 | 5/2016 | Jaffer et al. | |
| 9,513,276 B2 | 12/2016 | Tearney et al. | |
| 9,557,154 B2 | 1/2017 | Tearney et al. | |
| 2002/0198457 A1 | 12/2002 | Tearney et al. | |
| 2005/0165315 A1 | 7/2005 | Zuluaga et al. | |
| 2007/0236700 A1* | 10/2007 | Yun .................. | G01N 21/4795 356/491 |
| 2010/0092389 A1 | 4/2010 | Jaffer | |
| 2011/0292400 A1 | 12/2011 | Fleming et al. | |
| 2012/0101374 A1 | 4/2012 | Tearney et al. | |
| 2013/0271757 A1 | 10/2013 | Kang et al. | |
| 2013/0321819 A1* | 12/2013 | Lim .................. | G01B 9/02083 356/479 |
| 2015/0378105 A1 | 12/2015 | Godbout et al. | |
| 2017/0135584 A1 | 5/2017 | Tearney et al. | |
| 2017/0209049 A1 | 7/2017 | Wang et al. | |

FOREIGN PATENT DOCUMENTS

| | | |
|---|---|---|
| WO | 2015192886 A1 | 12/2015 |
| WO | 2016/077252 A1 | 5/2016 |

OTHER PUBLICATIONS

Yelin, D., et al., "Three-dimensional miniature endoscopy", Nature, Oct. 19, 2006, pp. 765, vol. 443.

\* cited by examiner

DEVICES, SYSTEMS, METHODS AND STORAGE MEDIUMS USING FULL RANGE OPTICAL COHERENCE TOMOGRAPHY

CROSS-REFERENCE TO RELATED APPLICATION(S)

This application claims priority to U.S. Provisional Application Ser. No. 62/347,246 filed 8 Jun. 2016, the content of which is incorporated herein by reference in its entirety.

FIELD OF THE INVENTION

The present disclosure relates generally to the field of optical imaging and more particularly to devices, systems, methods and storage mediums using full range optical coherence tomography (OCT). Examples of such applications include imaging, evaluating and diagnosing biological objects, such as, but not limited to, for cardio and/or ophthalmic applications, and being obtained via one or more optical instruments, such as, but not limited to, optical probes (e.g., common path probes), catheters, endoscopes, phase shift units (e.g., galvanometer scanner) and bench top systems.

BACKGROUND OF THE INVENTION

Optical coherence tomography (OCT) is a technique for obtaining high resolution cross-sectional images of tissues or materials, and enables real time visualization. The aim of the OCT techniques is to measure the time delay of light by using interferometry, such as via Fourier Transform or Michelson interferometers. A light from a light source delivers and splits into a reference arm and a sample (or measurement) arm with a splitter. A reference beam is reflected from a reference mirror (or other reflecting element) in the reference arm while a sample beam is reflected or scattered from a sample in the sample arm. Both beams combine (or are recombined) at the splitter and generate interference patterns. The output of the interferometer is detected with one or more detectors such as photodiodes or multi-array cameras, such as, but not limited to, in a spectrometer (e.g., a Fourier Transform infrared spectrometer). The interference patterns are generated only when the path length of the sample arm matches that of the reference arm to within the coherence length of the light source. By evaluating the output beam, a spectrum of an input radiation may be derived as a function of frequency.

The frequency of the interference patterns corresponds to the distance between the sample arm and the reference arm. The higher frequencies are, the more the path length differences are. The Fourier transforms are performed in order to obtain frequency distributions of the interference patterns to obtain axial back-scattering images. The reconstructed images are symmetric with respect to the zero delay of the interferometer, in other words, the longer arm and/or the shorter arm of both of the arms cannot be distinguished because of a real function of the detected interferometer patterns. To avoid complex mirror artifacts due to this ambiguity between the longer arm and the shorter arm, the zero delay is positioned outside of the images. Then, only half of imaging depth is available. In general, the sensitivity is highest around a zero delay position so that a signal to noise ratio (SNR) would be worse if the zero delay is positioned outside of the images.

However, previous attempts to overcome such complex mirror artifacts have not taken care of continuity of A-lines between frames. Because modulators are driven by saw-tooth waveform, response time is needed while operating from peak to bottom. Therefore, discontinuity from frame to frame happens, as shown in FIG. 1.

Accordingly, it would be desirable to provide at least one OCT technique for use in at least one optical device, assembly or system to achieve constant, stable A-lines over a sufficient predetermined period of time at high efficiency and a reasonable cost of manufacture and maintenance.

SUMMARY OF THE INVENTION

Accordingly, it is a broad object of the present disclosure to provide a further continuously full-range OCT technique without losing A-lines. Indeed, one aspect of the present disclosure is to provide continuity, from frame to frame, of A-lines.

The OCT technique may be used in at least one device, such as, but not limited to, a Fourier spectrometer, one or more optical probes (e.g., common path probes), one or more catheters, one or more endoscopes, one or more galvanometer scanner phase shift units and one or more bench top systems, to create an optical spectrum from a light/radiation beam and/or an electrical signal created from the light/radiation beam. Indeed, it is a further object of the present disclosure to provide an improved performance and continuously full-range OCT without losing A-lines as described herein.

In accordance with at least one aspect of the present disclosure, one or more embodiments of a continuously full-range optical coherence tomography system for continuously acquiring A-line data may include: a light source that operates to produce a light; an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and/or to interfere, with each other, the interference light generating one or more interference patterns; and one or more detectors that operate to continuously acquire the interference light and/or the one or more interference patterns such that continuous A-lines are obtained and to measure the interference or the one or more interference patterns between the combined or recombined light.

Preferably, in at least one embodiment, the one or more detectors obtain continuous A-lines such that continuous images of the object or sample are obtained without losing one or more A-lines and/or without occurring artifacts during signal processing.

The system may involve or include at least one of the following: (i) the interference optical system further includes a phase shift device that operates to apply phase modulation to a light passing therethrough; (ii) the phase modulation is applied with positive and negative constant frequency; (iii) the absolute value of the frequency is approximately a quarter of an A-line rate, which is the rate to acquire an axial OCT profile; and (iv) the phase shift device sinusoidally modulates the interference or the interference patterns. In one or more embodiments, a phase shift device may include a fiber, a collimator lens, a galvanometer scanner having a scanning mirror, and a focusing lens, wherein the fiber sends the light passing therethrough through the collimator lens to produce a collimated light beam from the collimator lens, the collimated light beam is reflected at an offset from a pivot point of the galvanometer scanner to and through the focusing lens to reflect off of the reference mirror or off of the object or sample and be transmitted back through the focusing lens, off of the galvanometer scanner, through the collimator lens and back into the fiber. In one or more embodiments, the phase shift device may be disposed in a reference arm of the interference optical system, the reference mirror may further operate to reflect the second reference light back through the phase shift device; and the phase shift device may operate to apply the phase modulation to or in the reference light passing therethrough. In one or more embodiments, the phase shift device may be disposed in a sample arm of the optical interference system; the light passing through the phase shift device may be the first light; the object or sample may reflect the first light through the focusing lens of the phase shift device; and the phase shift device may operate to apply the phase modulation to or in the first light passing therethrough.

The galvanometer scanner may be applied with or to a voltage with a triangle shape, the voltage having continuity or absolute constant frequency to at least one of: (i) obtain continuous images without losing any A-lines, (ii) avoid lost or dead A-lines from occurring during setting up positioning from frame to frame and (iii) modulate the optical path length linearly with time. A period of the galvanometer scanner may be synchronized with imaging frames and rotation speeds so that a single frame contains the modulation with either a positive or negative constant frequency of fm. An optical path length during scanning may change because the collimated light is reflected at the offset from the pivot point of the galvanometer scanner.

The focusing lens may be placed a focal length away from the galvanometer scanner and the reference mirror or the object or sample, and the collimated light beam, during scanning, may focus on the scanning mirror of the galvanometer scanner and go back to couple into the fiber such that uniformity of optical power during scanning is achieved with high coupling efficiency. The collimator lens may be defocused to have high tolerance and uniformity during scanning.

One or more embodiments of a continuously full-range optical coherence tomography system may further include: (i) a first circulator; (ii) a second circulator; (iii) a patient interface device; (iv) a common path probe that: (a) receives light from the light source via the first circulator, the optical interference system and the patient interface device, and (b) sends both the first light and the second reference light, which pass through the common path probe to reduce and/or cancel one or more phase noises, back to the optical interference system through the patient interface device such that the optical interference system splits the first light to go to the first circulator and splits the second reference light to go to the second circulator; (v) a length adjustment section disposed in the reference arm; and (vi) a combiner that operates to: (a) receive the first light via the first circulator, (b) receive the reflected second reference light, after being sent through the phase shift device via the length adjustment section, and (c) combine the first light and the reflected second reference light for delivery to the one or more detectors.

One or more embodiments of a continuously full-range optical coherence tomography system may further include: a patient interface device and a catheter disposed in a sample arm of the interference optical system such that: (i) the first light passes through the patient interface device and the catheter to irradiate the object or the sample and (ii) the reflected or scattered light of the first light with which the object or sample has been irradiated passes through the catheter and the patient interface device to be combined or recombined, and/or to interfere, with the reflected second reference light. The catheter may include a sheath, a coil, a protector and an optical probe, and the catheter may be connected to the patient interface device such that the patient interface device operates to spin the coil of the catheter with pullback. The coil may deliver torque from a proximal end to a distal end thereof, and the coil may be fixed with or to the optical probe so that a distal tip of the optical probe also spins to see an omnidirectional view of the object or sample. Additionally or alternatively, the optical probe may be simultaneously translated longitudinally during the rotational spin resulting in a helical scanning pattern.

One or more embodiments of a continuously full-range optical coherence tomography system may further include: (i) a first circulator; (ii) a length adjustment section disposed in a reference arm that receives the second reference light from the optical interference system so that the second reference light reflects off of the reference mirror, via the length adjustment section; and (iii) a combiner that operates to: (a) receive the first light and the reflected second reference light via the first circulator and the optical interference system, and (b) combine the first light and the reflected second reference light for delivery to the one or more detectors.

The interference optical system may include at least one of: an interferometer and a beam splitter that operates to perform the division of the light from the light source into the first light and the second reference light, wherein the interferometer and/or the beam splitter cause the first light to pass into a sample arm of the interference optical system and cause the second reference light to pass into a reference arm of the interference optical system, and wherein the beam splitter or a light splitting component of the interferometer are positioned or disposed at an angle to the reference mirror, the one or more detectors and the object or sample.

The one or more detectors may include at least one of: one or more photodiodes and one or more multi-array cameras.

One or more embodiments of a continuously full-range optical coherence tomography system may further include at least one processor that operates to process a signal from the one or more detectors to acquire information of the object or sample.

In accordance with at least another aspect of the present disclosure, one or more embodiments of a method for performing continuous full-range optical coherence tomography ("OCT") using a continuous full-range OCT device or system having a light source, an interference optical system that operates to generate interference light and one or more interference patterns from a light from the light source that has been split into a first light with which an object or sample has been irradiated and a second reference light and one or more detectors may include: continuously acquiring, via the one or more detectors, the interference light and/or the one or more interference patterns such that continuous A-lines are obtained and to measure the interference or the one or more interference patterns. Preferably, in at least one embodiment, the one or more detectors obtain continuous A-lines such that continuous images of the object or sample are obtained without losing one or more A-lines and/or without occurring artifacts during signal processing.

Continuous full-range OCT may be performed with one or more features of the above-described device(s) or system (s). For example, phase modulation may be applied to a light passing through a phase shift device of an OCT device or system, wherein at least one of: (i) the phase modulation is applied with positive and negative constant frequency; (ii) the absolute value of the frequency is approximately a quarter of an A-line rate, which is the rate to acquire an axial OCT profile; and (iii) the phase shift device sinusoidally modulates the interference or the interference patterns. The phase shift device may include a fiber, a collimator lens, a galvanometer scanner having a scanning mirror, and a focusing lens, wherein the fiber sends the light passing therethrough through the collimator lens to produce a collimated light beam from the collimator lens, the collimated light beam is reflected at an offset from a pivot point of the galvanometer scanner to and through the focusing lens to reflect off of a reference mirror or off of the object or sample and be transmitted back through the focusing lens, off of the galvanometer scanner, through the collimator lens and back into the fiber. Continuous full-range OCT may be performed with at least one of: a patient interface device, a catheter and a common path probe, or may be performed in a bench top system.

In accordance with at least a further aspect of the present disclosure, one or more embodiments of a method for processing at least one interference or interference pattern signal generated from a continuous full-range optical coherence tomography ("OCT") device or system having a light source, an interference optical system that operates to generate interference light and one or more interference patterns from a light from the light source that has been split into a first light with which an object or sample has been irradiated and a second reference light and one or more detectors may include: continuously acquiring, via the one or more detectors of the OCT device or system, the interference light and/or the one or more interference patterns to generate the interference or interference pattern signal and such that continuous A-lines are obtained.

One or more embodiments of such methods may include at least one of the following features: the continuous acquisition step further comprises acquiring a 2D array of data and 2D background data, wherein the 2D background data is obtained without data from the first light with which an object or sample has been irradiated; performing background subtraction or time average 2D background subtraction on the 2D array of data by having the detected 2D array be subtracted with the 2D background data to reduce or minimize any DC noise and fixed pattern noises; remapping the data to k-space; performing Fourier transform along, to or with A-lines in the k-space; performing one or more Window functions along, to or with an A-scan direction; performing Fourier transform along, to or with a B-scan or rotational scanning direction to obtain a modulated spectrum by a phase shift device of the OCT device or system; applying a shifted Heaviside step Window function to have either a positive or negative modulated peak along, to or with the B-scan direction; performing Inverse Fourier along, to or with the same B-scan direction to have or create a complex 2D array of data; computing a power spectrum; performing coordinate transformation to display continuous OCT images; performing DC and fixed pattern noise reduction using a noise reduction algorism; recovering DC signals or components by performing interpolations after Fourier transform along, to or with the A-scan direction; shifting or rotating OCT images by a phase delay, modulated by a phase shift device, of each A-line of each of frames to compensate a different phase delay applied to each A-line; and performing dispersion compensation or correction after at least one of: (i) performing background subtraction or time average 2D background subtraction on a 2D array of data by having a detected 2D array be subtracted with 2D background data to reduce or minimize any DC noise and fixed pattern noises; (ii) performing DC and fixed pattern noise reduction using a noise reduction algorism; and (iii) applying a shifted Heaviside step Window function to have either a positive or negative modulated peak along, to or with the B-scan direction.

In accordance with yet a further aspect of the present disclosure, one or more computer-readable storage mediums may be employed with one or more of the OCT devices, systems and/or methods discussed herein. For example, a computer-readable storage medium may store a program that operates to cause one or more processors to perform a method for performing continuous full-range optical coherence tomography using a continuous full-range OCT device or system having a light source, an interference optical system that operates to generate interference light and one or more interference patterns from a light from the light source that has been split into a first light with which an object or sample has been irradiated and a second reference light and one or more detectors, the method including: continuously acquiring, via the one or more detectors, the interference light and/or the one or more interference patterns such that continuous A-lines are obtained and to measure the interference or the one or more interference patterns.

According to other aspects of the present disclosure, one or more additional devices, one or more systems, one or more methods and one or more storage mediums using full range OCT are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

One or more devices, optical systems, methods and storage mediums for using a full range OCT technique are disclosed herein. In accordance with at least one aspect of the present disclosure, one or more devices, optical systems, methods and storage mediums discussed herein use a full range OCT technique without losing A-lines.

Figure 2:
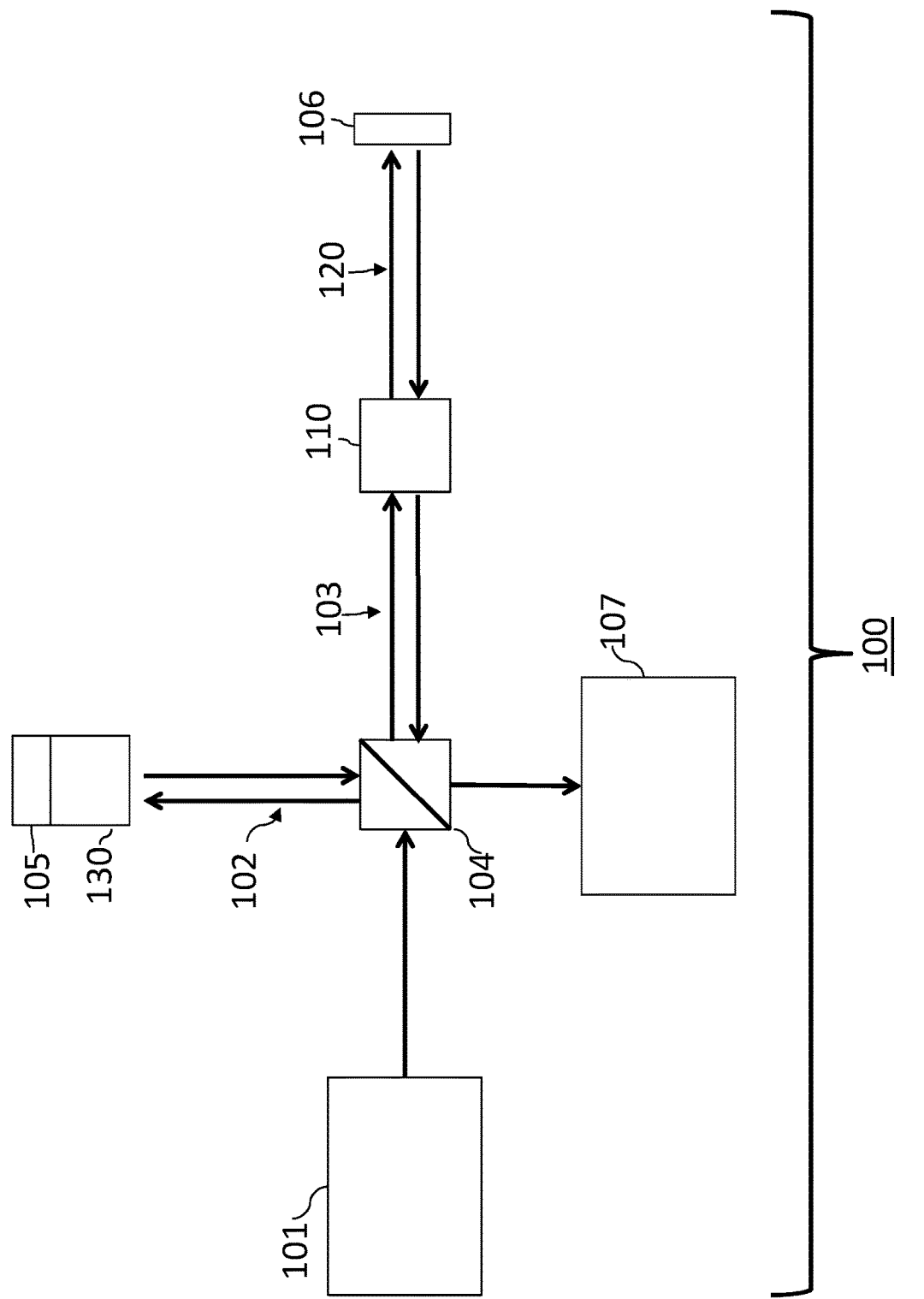
FIG. 2 is a diagram showing an embodiment of a system which can utilize a full-range OCT technique with optical probe applications in accordance with one or more aspects of the present disclosure.

Turning now to the details of the figures, FIG. 2 shows a continuous acquisition system 100 (as referred to herein as "system 100" or "the system 100") which operates to utilize a continuous full-range OCT technique with optical probe applications in accordance with one or more aspects of the present disclosure. The system 100 comprises a light source tot, a reference arm 102, a sample arm 103, a splitter 104 (also referred to herein as a "beam splitter"), a reference mirror 105, one or more detectors 107 and a phase shift device or unit 130. In one or more embodiments, the system 100 may include a patient interface device or unit ("PIU") 110 and a catheter 120 (as diagrammatically shown in FIG. 2; an embodiment example is shown in FIG. 3 and discussed further below), and the system 100 may interact with a sample 106 (e.g., via the catheter 120 and/or the PIU 110). In one or more embodiments, the system 100 includes an interferometer or an interferometer is defined by one or more components of the system 100, such as, but not limited to, at least the light source tot, the reference arm 102, the sample arm 103, the splitter 104 and the reference mirror 105.

The light source tot operates to produce a light to the splitter 104, which splits the light from the light source tot into a reference beam passing into the reference arm 102 and a sample beam passing into the sample arm 103. The beam splitter 104 is positioned or disposed at an angle to the reference mirror 105, the one or more detectors 107 and to the sample 106. The reference beam goes through the phase shift unit 130, and the reference beam is reflected from the reference mirror 105 in the reference arm 102 while the sample beam is reflected or scattered from a sample 106 through the PIU (patient interface unit) 110 and the catheter 120 in the sample arm 103. Both of the reference and sample beams combine (or recombine) at the splitter 104 and generate interference patterns. The output of the system 100 and/or the interferometer thereof is continuously acquired with the one or more detectors 107, e.g., such as, but not limited to, photodiodes or multi-array cameras. The one or more detectors 107 measure the interference or interference patterns between the two radiation or light beams that are combined or recombined. In one or more embodiments, the reference and sample beams have traveled different optical path lengths such that a fringe effect is created and is measurable by the one or more detectors 107. Electrical analog signals obtained from the output of the system 100 and/or the interferometer thereof are converted to digital signals to be analyzed with a computer, such as, but not limited to, the computer 1200 (shown in FIG. 12 discussed further below). In one or more embodiments, the light source tot may be a radiation source or a broadband light source that radiates in a broad band of wavelengths. In one or more embodiments, a Fourier analyzer including software and electronics may be used to convert the electrical analog signals into an optical spectrum.

Figure 3A:
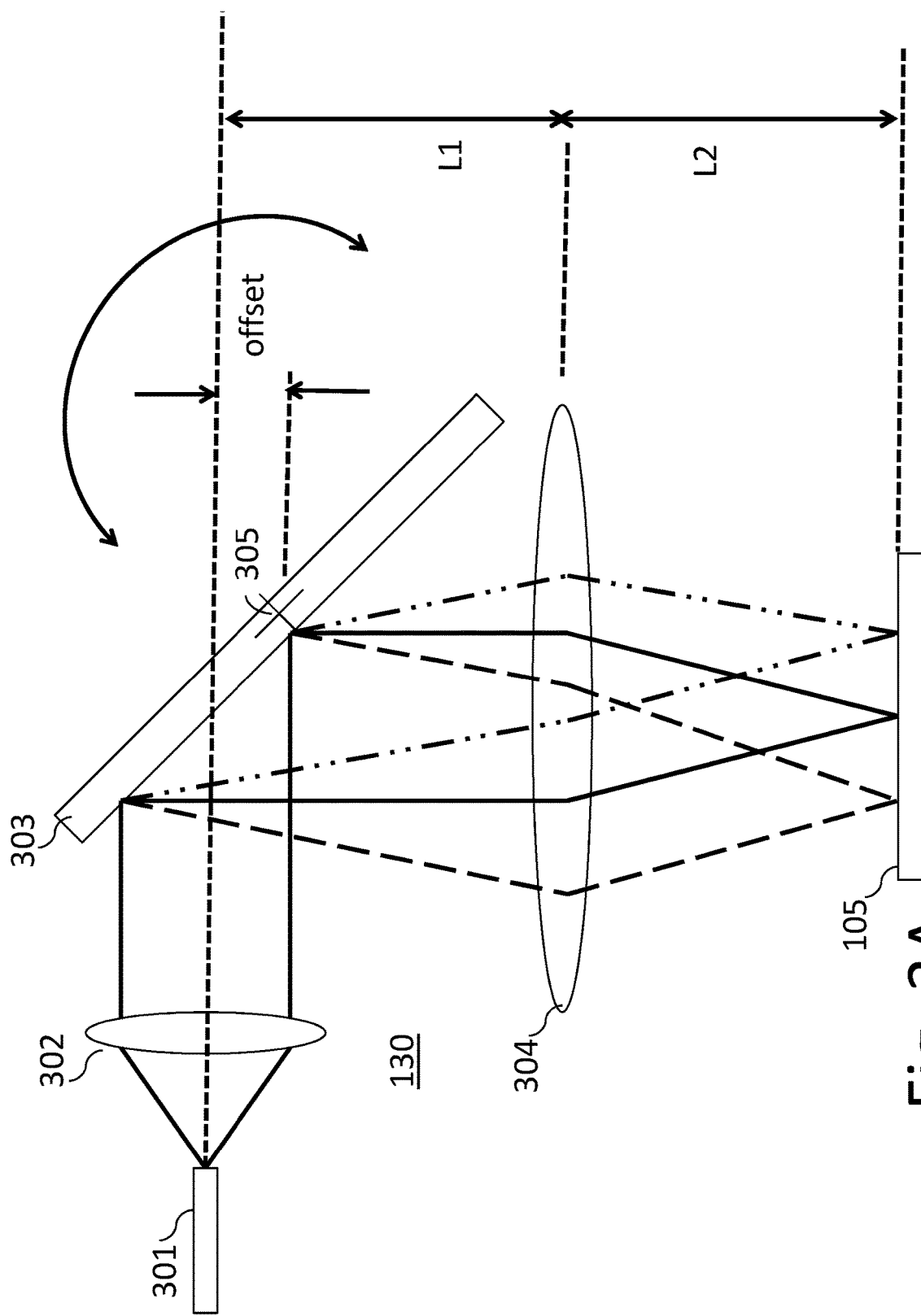
FIG. 3A shows an example of a phase shift unit and a reference mirror that may be used with at least one embodiment of a full-range OCT technique with optical probe applications in accordance with one or more aspects of the present disclosure.

At least one embodiment of a phase shift unit, such as the phase shift unit 130 (shown schematically in FIG. 2), and a reference mirror, such as the reference mirror 105, is shown in FIG. 3A. The phase shift unit 130 has a function to apply phase modulation in the reference beam. The phase modulation is applied with positive and negative constant frequency. The absolute value of the frequency is approximately a quarter of an A-line rate, which is the rate to acquire an axial OCT profile. For example, in at least one embodiment, when the A-line rate is 100 kHz in at least one embodiment, the phase shift unit 130 is operated to have the frequency of approximately 25 kHz to minimize the complex mirror artifacts.

As shown in FIG. 3A, at least one embodiment of the phase shift unit 130 includes a fiber 301, a collimator lens 302, a galvanometer scanner (also referred to as a scanning mirror) 303, and a focusing lens 304, and the phase shift unit 130 interacts with the reference mirror 105 to reflect light therebetween. The collimated beam from the collimator lens 302 is reflected at the offset from a pivot point 305 of the galvanometer scanner 303. Then, the beam focuses on the mirror 105 through the focusing lens 304. The focusing lens 304 is placed the focal length away (f) from the galvanometer scanner 303 and the mirror 105 (L1, L2 as shown in FIG. 3A and f are approximately the same) so that the beam during scanning focuses on the scanning mirror 303 and goes back to couple into the fiber 301. Therefore, uniformity of optical power during scanning is achieved with high coupling efficiency. It may be applied, in one or more embodiments, to defocus the collimator lens 302 in order to have high tolerance and uniformity during scanning.

Preferably, the galvanometer scanner 303 is applied with triangle shape voltage, which does not have discontinuity. Therefore, dead A-lines do not occur during setting up positioning from frame to frame, and continuous images without losing A-lines are obtained. In one or more embodiments, absolute constant frequency with the triangle shape voltage is achieved; therefore, the optical path length is modulated linearly with time. Preferably, in one or more embodiments, employing the triangle shape voltage involves+ and − signal processing. Preferably, the interference signals are sinusoidally modulated with the phase shift unit 130. In one or more embodiments, the galvanometer scanner 303 may include an offset as shown, for example, in FIGS. 3A-3B and 11. For example, as shown in FIG. 3B, the offset may be 3 mm.

Figure 5:
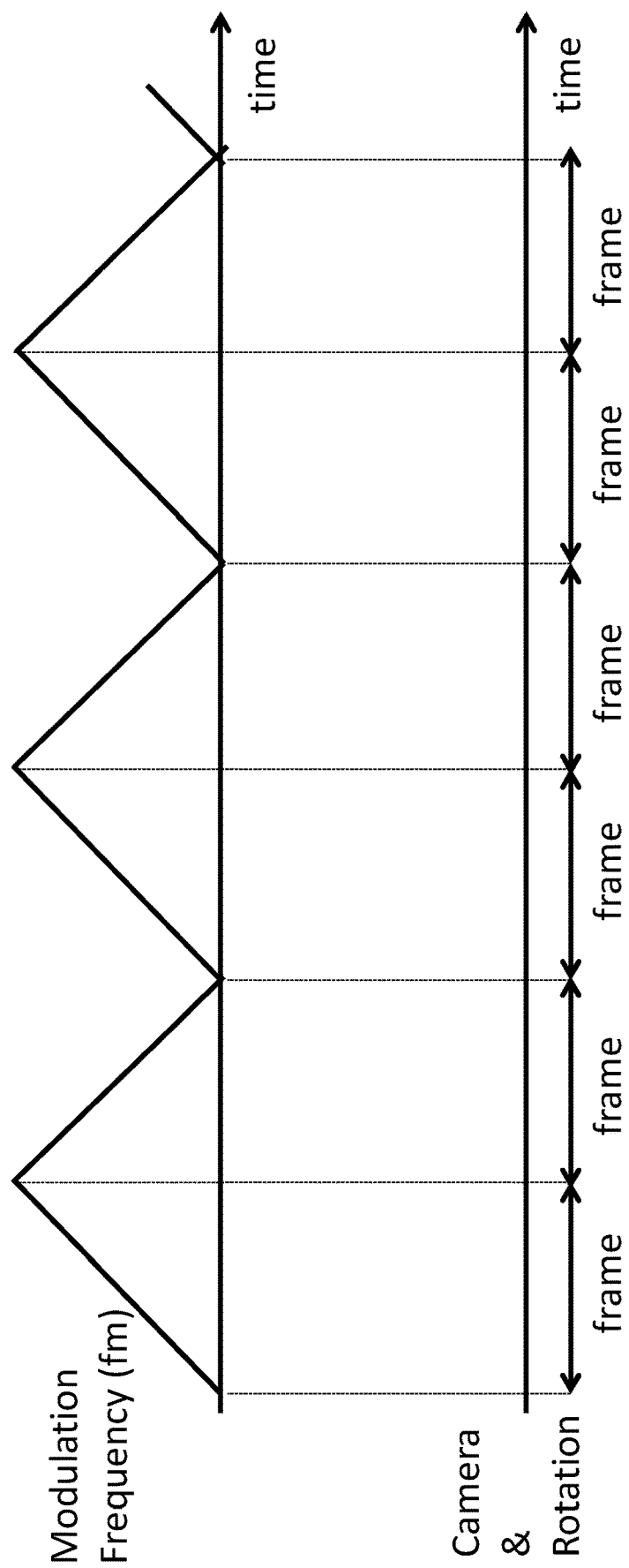
FIG. 5 is a diagram showing an embodiment of a modulation frequency for at least a full-range OCT in accordance with one or more aspects of the present disclosure that maintains continuity of A-lines between frames over time.

Regarding device communication, the period of the galvanometer scanner 303 of the phase shift unit 130 preferably is synchronized with imaging frames and rotation speeds so that a single frame contains the modulation with either positive or negative constant frequency of fm, by way of at least one example, as shown in FIG. 5. In one or more embodiments, continuous OCT images are obtained without occurring artifacts during signal processing as discussed further below.

Figure 3B:
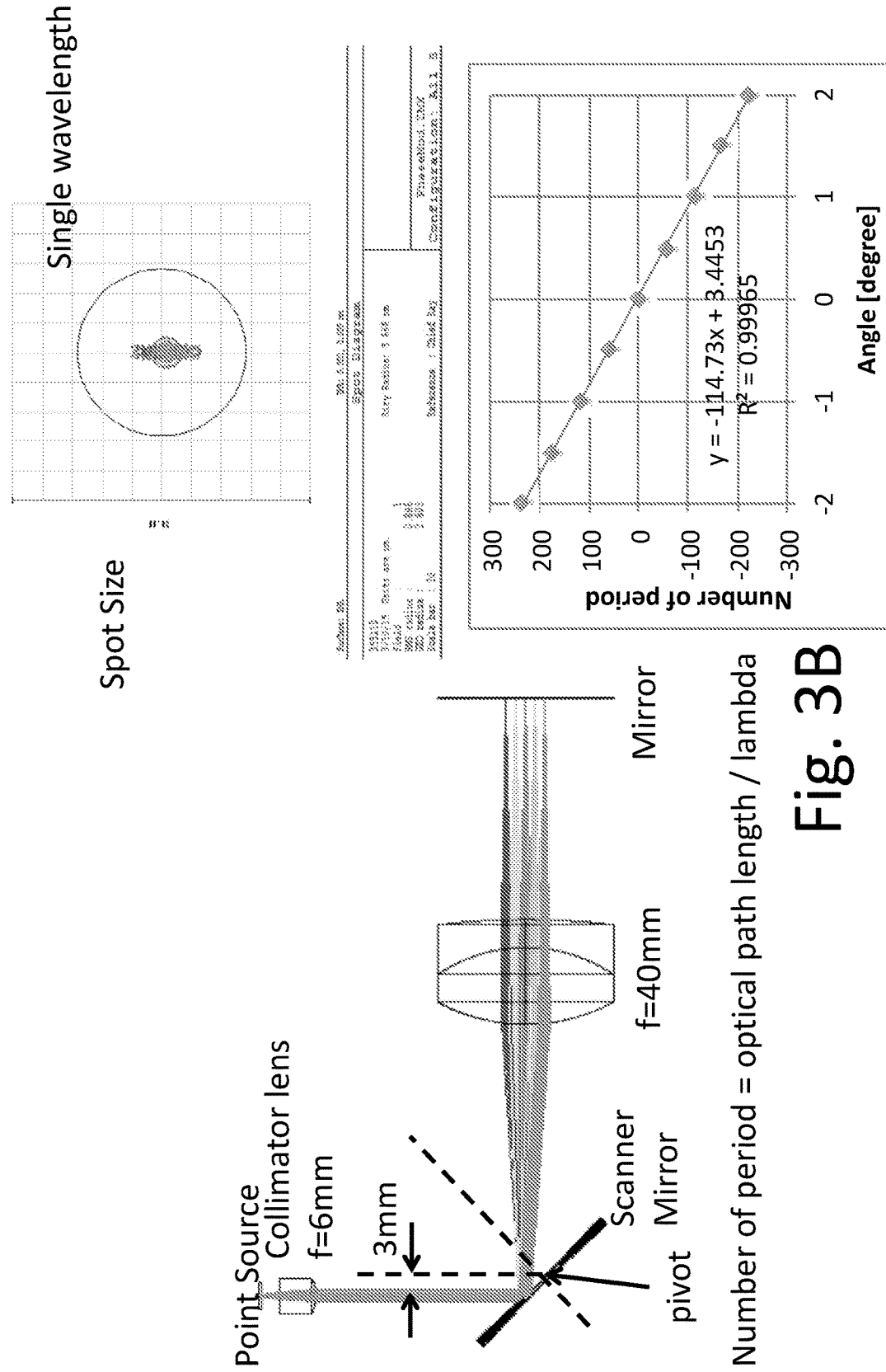
FIG. 3B shows a Zemax simulation for an embodiment of a phase shift unit and a reference mirror that may be used with at least one embodiment of a full-range OCT technique in accordance with one or more aspects of the present disclosure.

Additionally, FIG. 3B illustrates a Zemax simulation for an embodiment of a phase shift unit, such as the phase shift unit 130, and a reference mirror, such as the reference mirror 105, that may be used with at least one embodiment of a full-range OCT technique in accordance with one or more aspects of the present disclosure. Among the data of the Zemax simulation shown in FIG. 3B, a spot diagram is included showing spot size (single wavelength). The units are shown in micrometers (μm). Zemax shows an RMS-radius value in the spot diagram of 0.886 μm, a GEO radius of 2.603 μm and an Airy radius of 5.666 μm. The scale bar was set at 20. Also included in FIG. 3B is a graph plotting a number of periods versus angle (in degrees), where the number of periods is equal to −114.73×the angle (in degrees)+3.4453 and where $R^2$=0.99965. The number of period(s) is equal to an optical path length divided by lambda (λ or the wavelength). In one or more embodiments, the linear phase modulation is achieved with the phase shift unit 130 (e.g., the phase shift unit 130 works linear modulation properly). Further included in FIG. 3B is a schematic diagram of the specific measurements of the phase unit 130 undergoing the Zemax simulation. The focal length of the collimator lens (e.g., the collimator lens 302) was 6 mm, and the focal length of the focusing lens (e.g., the focusing lens 304) was 40 mm.

Figure 4:
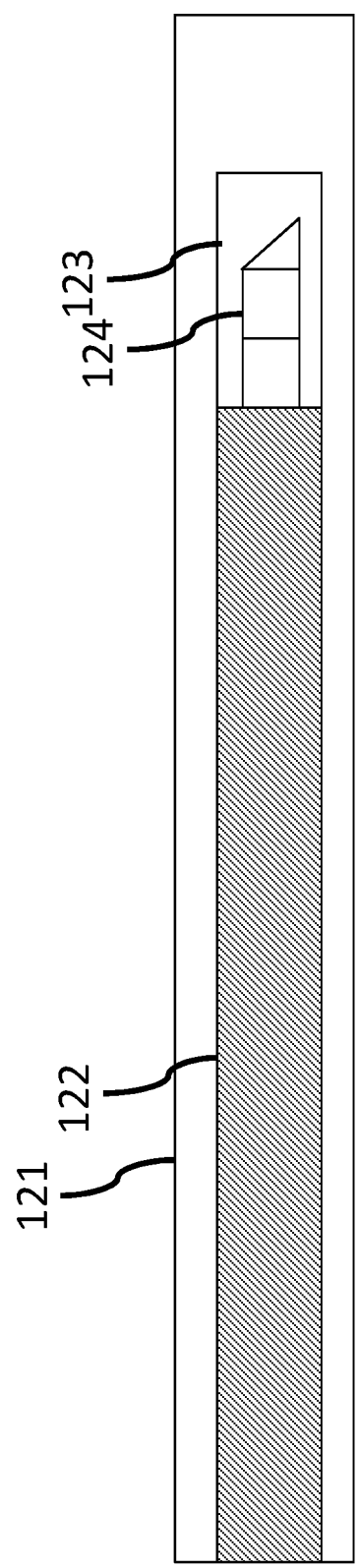
FIG. 4 is a diagram of an embodiment of a catheter that may used with at least one embodiment of a full-range OCT technique with optical probe applications in accordance with one or more aspects of the present disclosure.

In accordance with at least one aspect of the present disclosure, a feature of continuous full-range OCT systems is implemented using fiber optics. As aforementioned, one application of a full-range OCT technique of the present disclosure is to use with the catheter 120 as schematically shown in FIG. 2. FIG. 4 shows an embodiment of the catheter 120 including a sheath 121, a coil 122, a protector 123 and an optical probe 124. As shown schematically in FIG. 2, the catheter 120 preferably is connected to the PIU 110 to spin the coil 122 with pullback (e.g., at least one embodiment of the PIU 110 operates to spin the coil 122 with pullback). The coil 122 delivers torque from a proximal end to a distal end thereof. In one or more embodiments, the coil 122 is fixed with/to the optical probe 124 so that a distal tip of the optical probe 124 also spins to see an omnidirectional view of a biological organ, sample or material being evaluated, such as, but not limited to, hollow organs such as vessels, a heart, etc. For example, fiber optic catheters and endoscopes may reside in the sample arm (such as the sample arm 103 as shown in FIG. 2) of an OCT interferometer in order to provide access to internal organs, such as intravascular images, gastro-intestinal tract or any other narrow area, that are difficult to access. As the beam of light through the optical probe 124 inside of the catheter 120 or endoscope is rotated across the surface of interest, cross-sectional images of one or more samples are obtained. In order to acquire three-dimensional data, the optical probe 124 is simultaneously translated longitudinally during the rotational spin resulting in a helical scanning pattern. This translation is most commonly performed by pulling the tip of the probe 124 back towards the proximal end and therefore referred to as a pullback.

Figure 1:
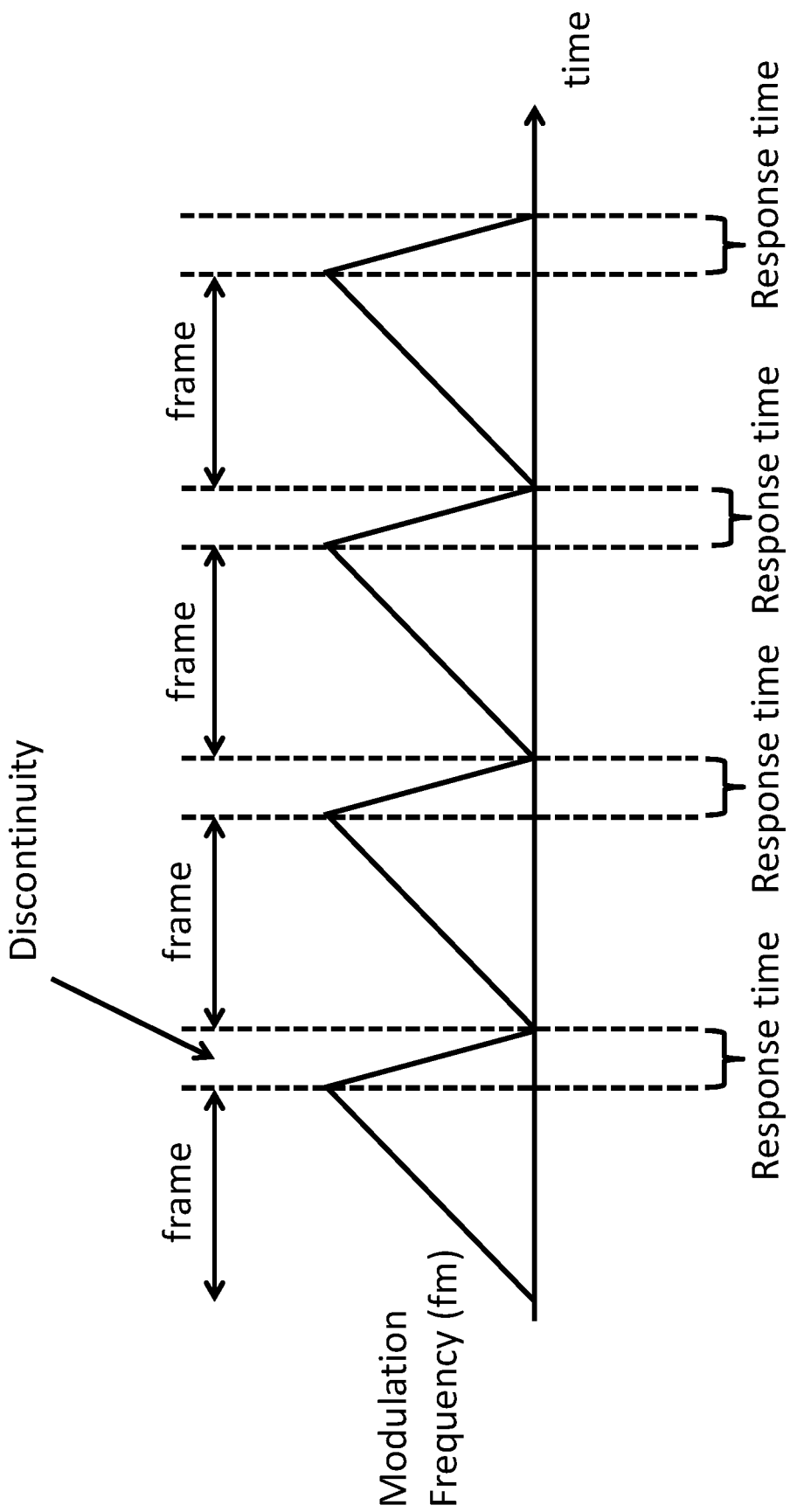
FIG. 1 is a diagram showing an example of a modulation frequency for at least one OCT device that does not maintain continuity of A-lines between frames over time.

Not only are the devices, systems, methods and storage mediums described herein unique, but the various aspects of the present disclosure are also nonobvious. Specifically, classical methods are not capable of acquiring continuous A-line data and include discontinuities (see e.g., FIG. 1) as aforementioned. However, various aspects of the present disclosure are not limited by inefficient response time, and provide continuous A-lines, from frame to frame, and continuous acquisition of OCT images.

Figure 6:
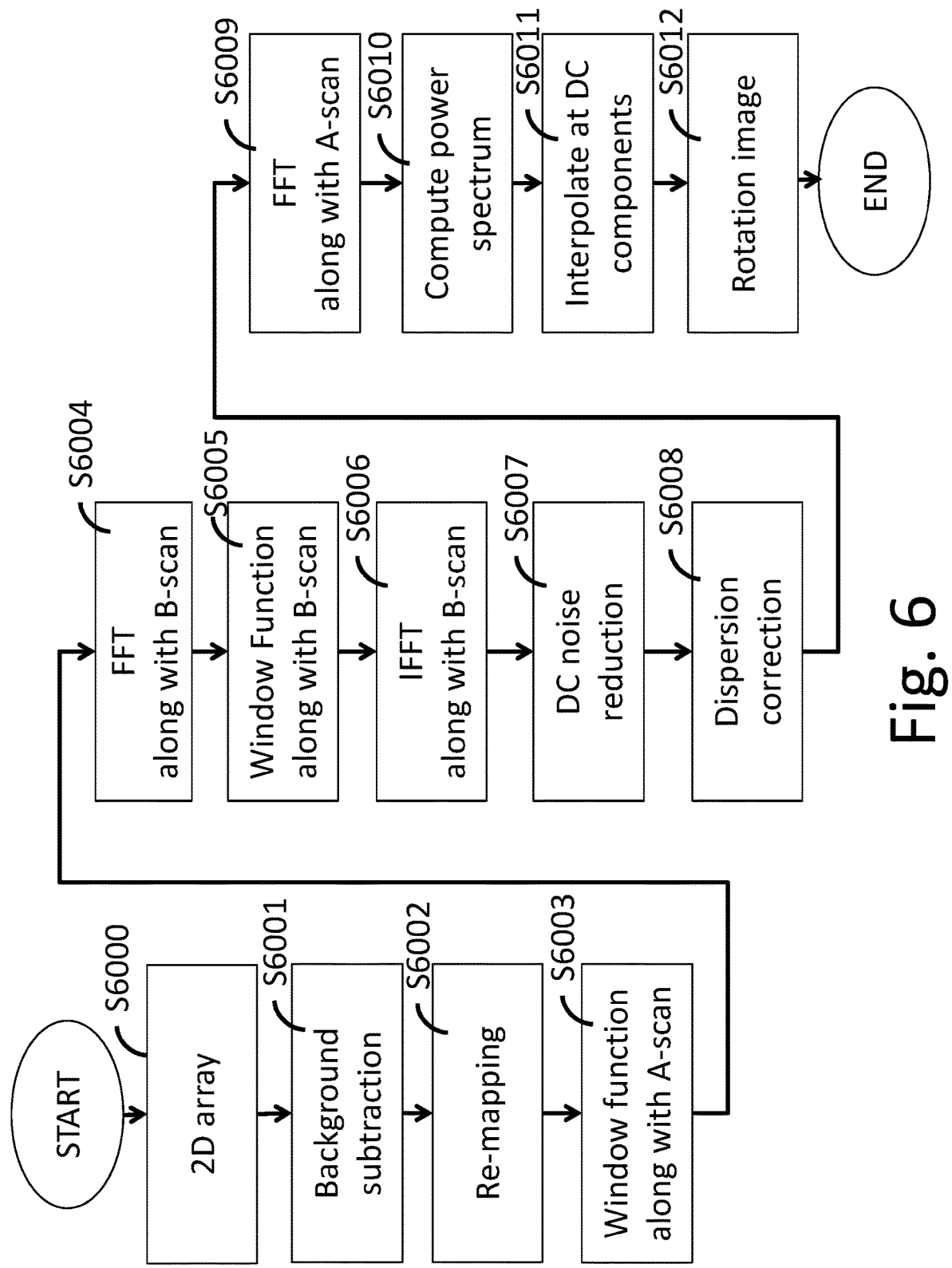
FIG. 6 is a flow diagram showing an embodiment of signal processing in accordance with one or more aspects of the present disclosure.

In accordance with another aspect of the present disclosure and as aforementioned, one or more methods for performing signal processing are provided herein to achieve continuous acquisition of OCT images without occurring artifacts. FIG. 6 illustrates a flow chart of at least one embodiment of a method for performing signal processing. Preferably, the method(s) may include one or more of the following: (i) acquiring, via one or more detectors (such as the one or more detectors 107), a 2D array of data (e.g., acquisition may be during single rotation by the PIU no) (see step 6000 of FIG. 6); (ii) background subtraction (e.g., with 2D array background data, time average 2D data background subtraction, etc.) (see step S6001 of FIG. 6); (iii) re-mapping to k-space (see step S6002 of FIG. 6); (iv) one or more Window functions (along, to or with an A-scan direction) such as hanning or hamming are applied, respectively, as necessary (see step S6003 of FIG. 6); (v) performing Fourier transform (e.g., FFT or Fast Fourier Transform) along, to or with a B-scan (rotational scanning) direction are performed to obtain a modulated spectrum by the phase shift unit 130 (see step S6004 of FIG. 6); (vi) applying a Window function (e.g., a shifted Heaviside step Window function to have either a positive or negative modulated peak) along, to or with the B-scan direction (see step S6005 of FIG. 6); (vii) performing Inverse Fourier transform (e.g., IFFT or Inverse Fast Fourier Transform) along, to or with the same B-scan direction to have or create a complex 2D array of data (see Step S6006 of FIG. 6); (viii) performing Fourier transform (e.g., FFT or Fast Fourier Transform) along, to or with A-lines (k-space) (see step S6009 of FIG. 6); (ix) computing the power spectrum (see step S6010 of FIG. 6); and (x) performing coordinate transformation to display OCT images as typical OCT processing (see step S6012 of FIG. 6 where one embodiment of coordinate transformation involves rotation of an image). One or more embodiments of methods discussed herein include all of steps (i)-(x) discussed above (i.e., steps S6000, S6001, S6002, S6003, S6004, S6005, S6006, S6009, S6010 and S6012 as shown in FIG. 6), and one or more further embodiments preferably include all of the steps shown in FIG. 6.

Additionally, one or more methods of signal processing may further include DC and fixed pattern noise reduction (see step S6007 of FIG. 6).

Figure 7:
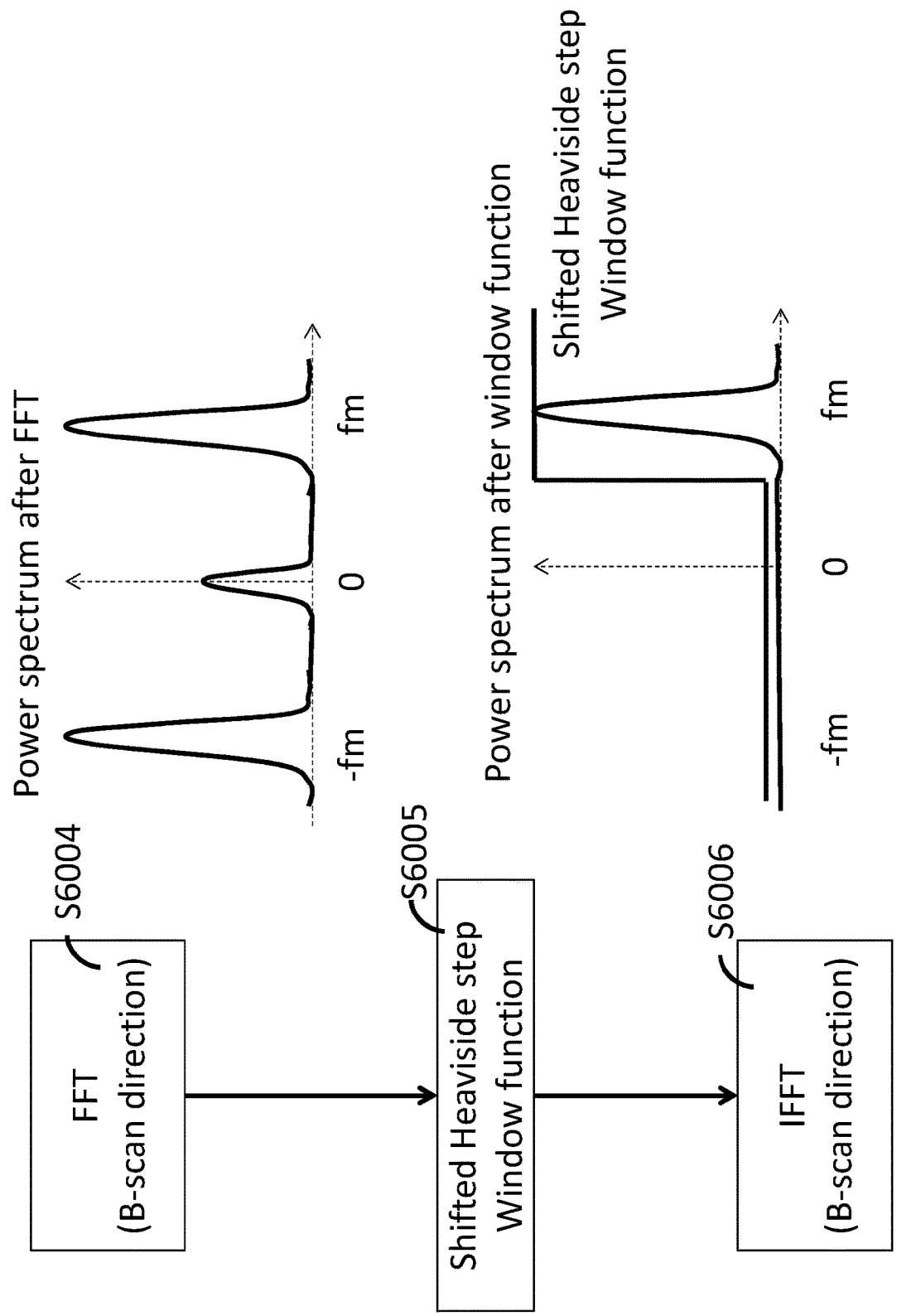
FIG. 7 shows a flow diagram, and related graphs of a power spectrum after Fourier Transform, showing an embodiment where a shifted Heaviside step Window function is multiplied to make negative modulated peaks and DC peak zero in accordance with one or more aspects of the present disclosure.

Preferably, background subtraction (S6001) with 2D array background data, the shifted Heaviside step Window function (as may be performed for S6005 as discussed above) and a DC noise reduction algorithm (S6007) are applied, in one or more embodiments, to reduce and/or minimize DC and fixed pattern noises. Preferably, the 2D background data is generated by averaging frames with at least 2 frames without the beam from the sample arm 103 before measuring. Then, a detected 2D array is subtracted with the 2D background data in order to reduce DC noise and the fixed pattern noises. The 2D background data is used for minimizing the fixed pattern noise from the phase shift unit 130 during scanning. Preferably, the shifted Heaviside step Window function (as may be performed for S6005 as discussed above) is applied to reduce the un-modulated DC and fixed pattern noises. After Fourier transform along, with or to the B-scan direction (S6004), the power spectrum has mainly three peaks, i.e., positive and negative modulated peaks with frequency of fm and a DC peak. Preferably, the shifted Heaviside step Window function (as may be performed for S6005 as discussed above) is multiplied to make the negative modulated peak(s) and the DC peak zero, as shown in FIG. 7. As a result, the un-modulated DC and fixed pattern noises corresponding to DC peak are reduced to utilize the shifted Heaviside step function.

Figure 8:
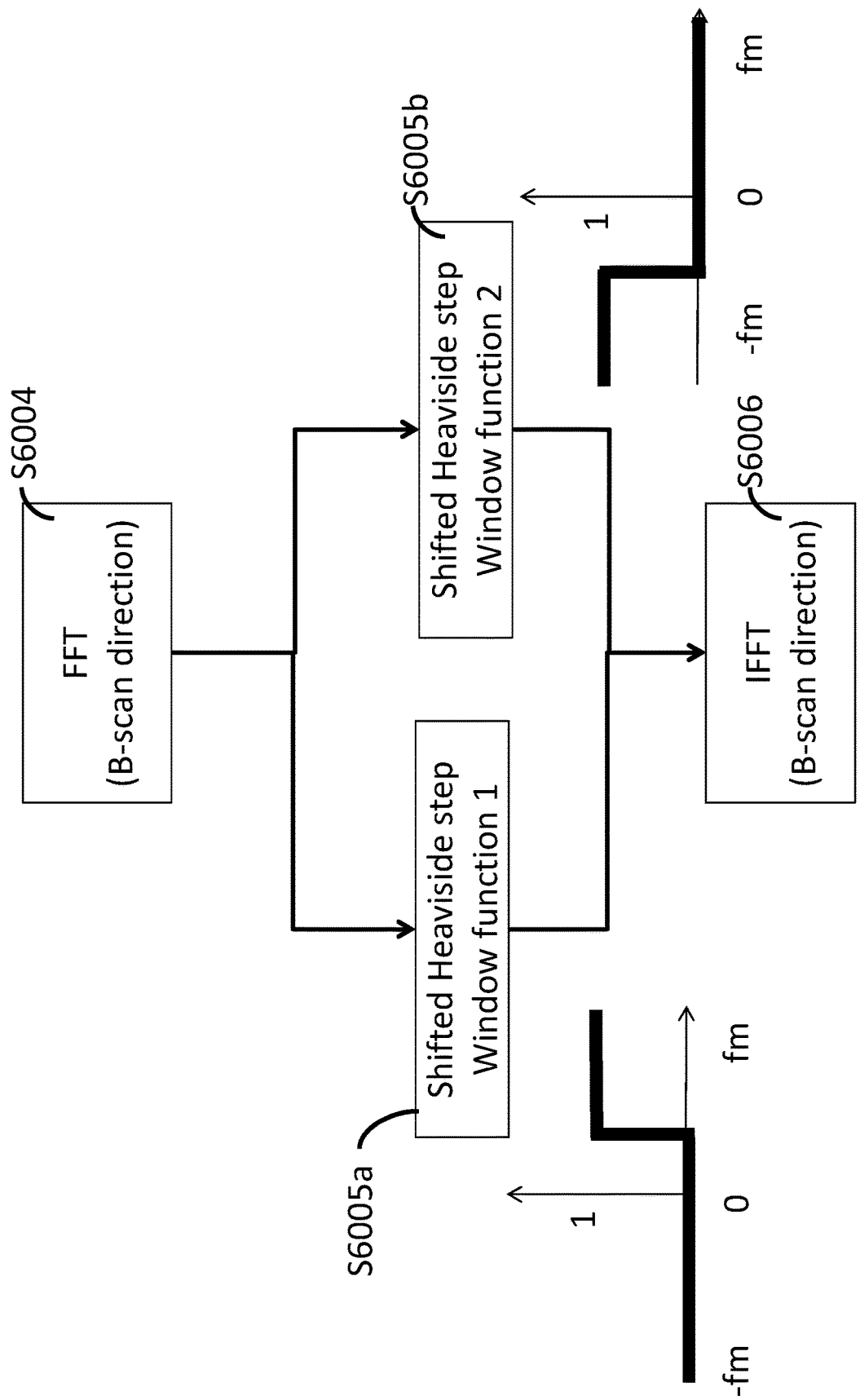
FIG. 8 shows a flow diagram, and related graphs, showing an embodiment where, when the polarity is negative, one Window function (e.g., Window function 2) is applied to keep a negative frequency of −fm and, when the polarity is positive, another Window function (e.g., Window function 1) is applied to keep a positive frequency of fm in accordance with one or more aspects of the present disclosure.

Turning to the details of FIG. 8, the shifted Heaviside step Window function (as may be performed for S6005 as discussed above) that may be applied may include or comprise two shifted Heaviside step Window functions 1 and 2 (see steps S6005a and S6005b of FIG. 8). The shifted Heaviside step Window functions 1 and 2 are multiplied in depending on the polarity of constant frequency of the triangle shape voltage. When the polarity is positive, the Window function 1 is applied to keep a positive frequency of fm (as best shown in the flowchart portion and in the power spectrum graph on the left side of FIG. 8). When the polarity is negative, the Window function 2 is applied to keep a negative frequency of −fm (as best shown in the flowchart portion and in the power spectrum graph shown on the right side of FIG. 8). The Window functions 1 and 2 have y-axis symmetry (as best seen in the two graphs included in FIG. 8 for each of the Window functions 1 and 2), and un-modulated DC and fixed pattern noises are reduced with both Window functions 1 and 2.

As aforementioned for step S6007, a DC noise reduction algorism (S6007) is preferably applied after Inverse Fourier transform (S6006). In one or more embodiments, each A-scan data is subtracted by averages of A-line complex data. The DC components including the DC noise become zero with this subtraction. DC signals or components are recovered with interpolations (see step S6011 of FIG. 6) after Fourier transform along, with or to the A-scan direction. In one or more embodiments, only DC signals without DC noises are recovered with the DC noise reduction algorism. Preferably the DC noise reduction algorism is applied before dispersion compensation or correction as discussed below.

Additionally or alternatively, dispersion correction (as best shown in step S6008 in FIG. 6) may be applied after background subtraction (step S6001), shifted Heaviside step Window function (e.g., step S6005) and DC noise reduction algorism (step S6007) as necessary. When dispersion correction is applied (step S6008), the DC and fixed pattern noises become broader. As such, to reduce the effect of and/or to minimize the broadening of such noises, the dispersion correction (step S6008) is preferably applied after minimizing the DC and fixed pattern noises. As such, difficulties in minimizing broadened noises may be avoided.

For image processing, at least one embodiment of the phase shift unit 130 modulates the phase delay along, with or to the B-scan direction. Therefore, each A-line of each of the frames is applied with different phase delay, which is corresponding to the optical path length. To compensate the different phase delay, images after signal processing are preferably rotated by the phase delay (see step S6012 of FIG. 6). The rotation (S6012) for compensation of the phase delay may be applied during signal processing after computing the power spectrum (S6010). As such, one or more embodiments of the present disclosure may employ image shifting to accommodate or compensate for the delay via modulation of the phase shift unit 130.

While the aforementioned embodiment(s) have bene discussed with respect to standard OCT and Fourier Transform techniques, other transform techniques may be additionally or alternatively employed, such as, but not limited to Hilbert transform. For example, in a standard OCT where raw data sampling frequency is 120 kHz, resampling (spline interpolation) may be performed, and thereafter Fourier transform (e.g., FFT or Fast Fourier Transform) may be performed along, with or to the A-line direction. As aforementioned, steps such as S6004-S6006 may be performed. For example, after resampling but before FFT along, with or to the A-line direction, FFT may be performed along, with or to the transverse or B-scan direction, a Heaviside step Window function may be performed and Inverse FFT (or IFFT) may be performed along, with or to the transverse or B-scan direction. Alternatively or additionally, after resampling but before FFT along, with or to the A-line direction, Hilbert transform may be performed along, with or to the transverse or B-scan direction.

Figure 9:
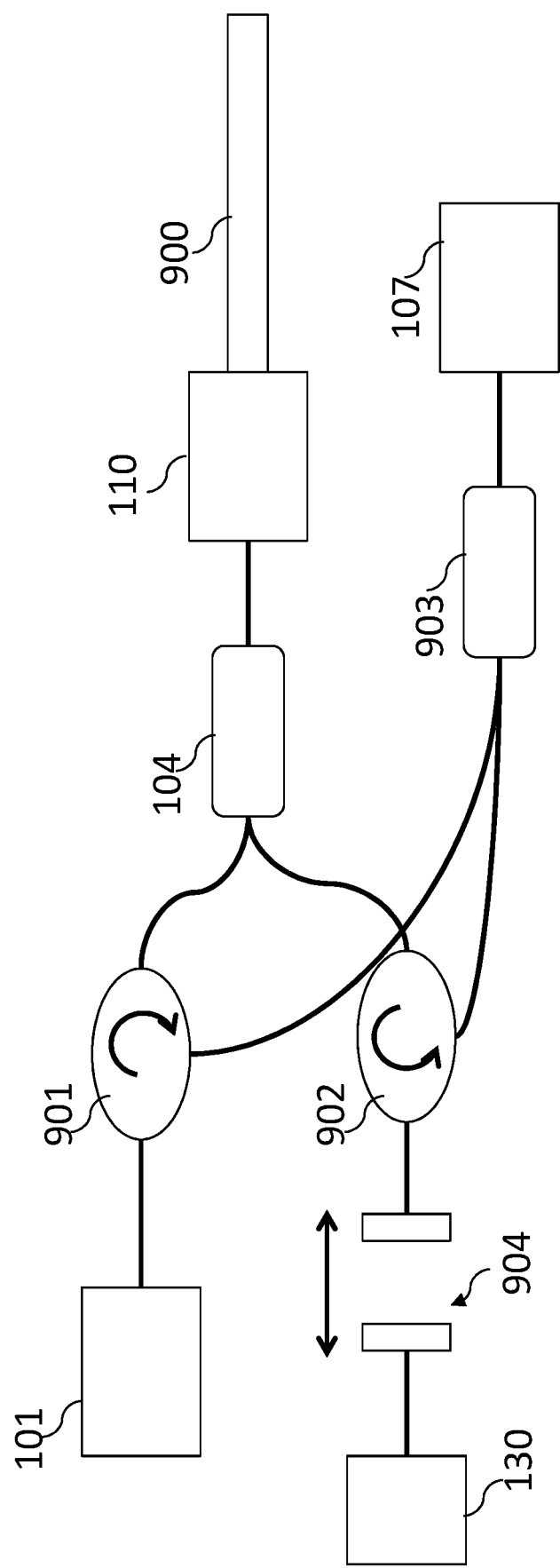
FIG. 9 shows a schematic diagram of an interferometer using a common path probe in accordance with one or more aspects of the present disclosure.

In accordance with one or more additional aspects of the present disclosure, common path probes may be utilized with the continuous full-range OCT techniques disclosed herein. Preferably, the reference beam of the reference arm 102 is modulated to achieve full-range OCT, and, therefore, the full-range OCT may be sensitive to phase fluctuations. Phase noises may be added while spinning a fiber probe, such as the optical probe 124 (shown in FIG. 4). As such, common path probes may be utilized to reduce such phase noises. To separate the reference and sample arms 102, 103 (see FIG. 2) with a common path probe, double interferometers are applied. FIG. 9 illustrates a schematic interferometer for use with a common path probe in accordance with the present disclosure. A light source 101 operates to deliver light into a common path probe 900 via a circulator 901, a splitter 104 and a PIU 110. Both a reference beam and a sample beam go back to the splitter 104 from the common path probe 900 through the PIU no. The beams are split and go to the circulator 901 and circulator 902. The beam via the circulator 901 delivers to a combiner 903. The beam via the circulator 902 goes to the phase shift unit 130 (which may include a reference mirror, such as the reference mirror 105, in one or more embodiments) via a length adjustment section 904 of the reference arm (e.g., reference arm 103), and then the beam goes to the combiner 903. The combiner 903 combines both beams via the circulator 901 and the circulator 902, and the combined beams are delivered to one or more detectors (such as the one or more detectors 107). The reference beam is reflected at a distal end of the common path probe 900. Therefore, both the sample and reference beams go through the optical probe 900, which make phase noises from an optical fiber canceled.

An optical probe distance between the reference optical path length and sample optical path length in the optical probe is approximately same as the distance between optical path 1 and optical path 2. Optical path 1 is an optical path length from the splitter 104 to the combiner 903 via the circulator 901. Optical path 2 is the path length from the splitter 104 to the combiner 903 via the circulator 902. When the reference optical path length is longer than the sample optical path length, optical path 1 is longer than optical path 2. When the reference optical path length is shorter than the sample optical path length, optical path 1 is shorter than optical path 2.

Figure 10:
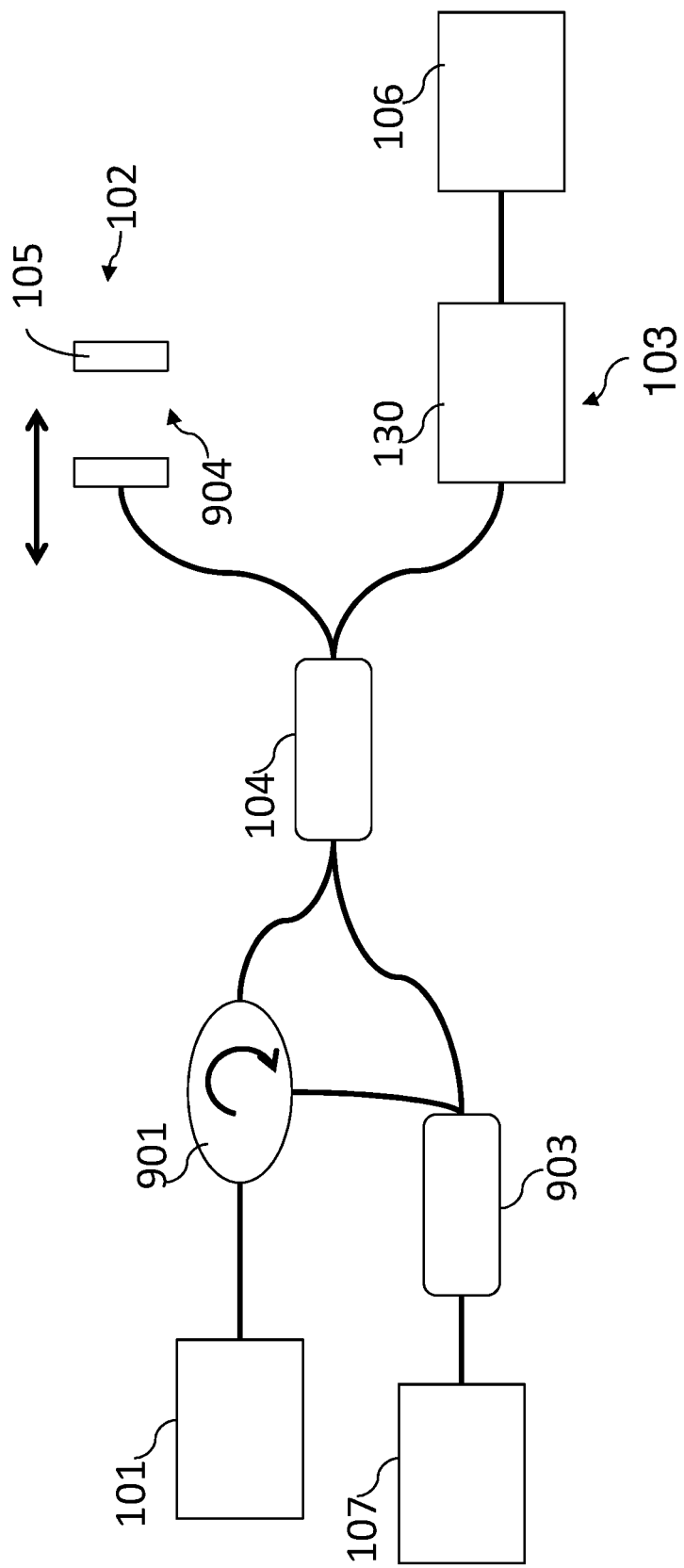
FIG. 10 illustrates a schematic diagram of an optical system that may be used with at least one embodiment of a continuous full-range OCT technique for a bench-top, such as, but not limited to ophthalmic applications in accordance with one or more aspects of the present disclosure.

In accordance with one or more further aspects of the present disclosure, bench top systems may be utilized with the continuous full-range OCT techniques disclosed herein. FIG. 10 shows an exemplary system that can utilize the continuous full-range OCT techniques for a bench-top such as for ophthalmic applications. A light from a light source 101 delivers and splits into a reference arm 102 and a sample arm 103 with a splitter 104. A reference beam goes through a length adjustment section 904 and is reflected from a reference mirror (such as reference mirror 105 shown in FIG. 2) in the reference arm 102 while a sample beam is reflected or scattered from a sample 106 through a phase shift unit (such as the phase shift unit 130) in the sample arm 103. In one embodiment, both beams combine at the splitter 104 and generate interference patterns. In one or more embodiments, the beams go to the combiner 903, and the combiner 903 combines both beams via the circulator 901 and the splitter 104, and the combined beams are delivered to one or more detectors (such as the one or more detectors 107). The output of the interferometer is continuously acquired with one or more detectors, such as the one or more detectors 107. The electrical analog signals are converted to the digital signals to analyze them with a computer.

Figure 11:
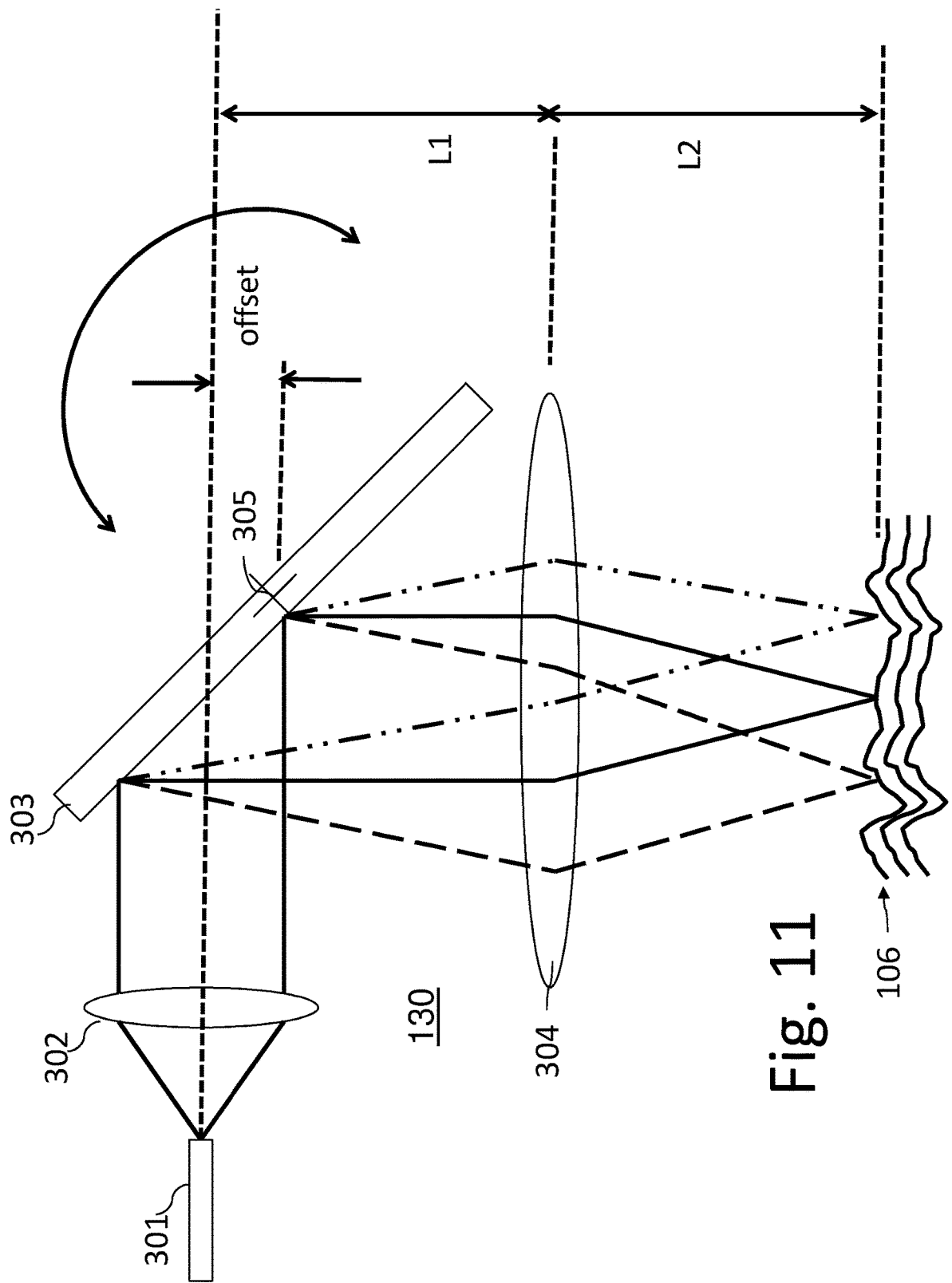
FIG. 11 shows an example of a phase shift unit that may be used with at least the embodiment of the optical system of FIG. to in accordance with one or more aspects of the present disclosure.

FIG. 11 shows the phase shift unit 130 for the bench top system(s) (e.g., the bench top system embodiment shown in FIG. 10). The sample 106 is located at the place of the mirror 105 used with the phase shift unit 130 as shown in FIG. 2. The optical path length during scanning changes because the collimated beam is reflected at the offset from the pivot point 305 of the galvanometer scanner 303. Similarly to the phase shift unit 130 of FIG. 2, a triangle shaped voltage is applied to the galvanometer scanner 303 to continuously acquire all A-lines to construct full-range OCT images.

There are many ways to compute power, digital as well as analog. In at least one embodiment, a computer may be dedicated to the control and the monitoring of the OCT devices, systems, methods and/or storage mediums described herein.

Figure 12:
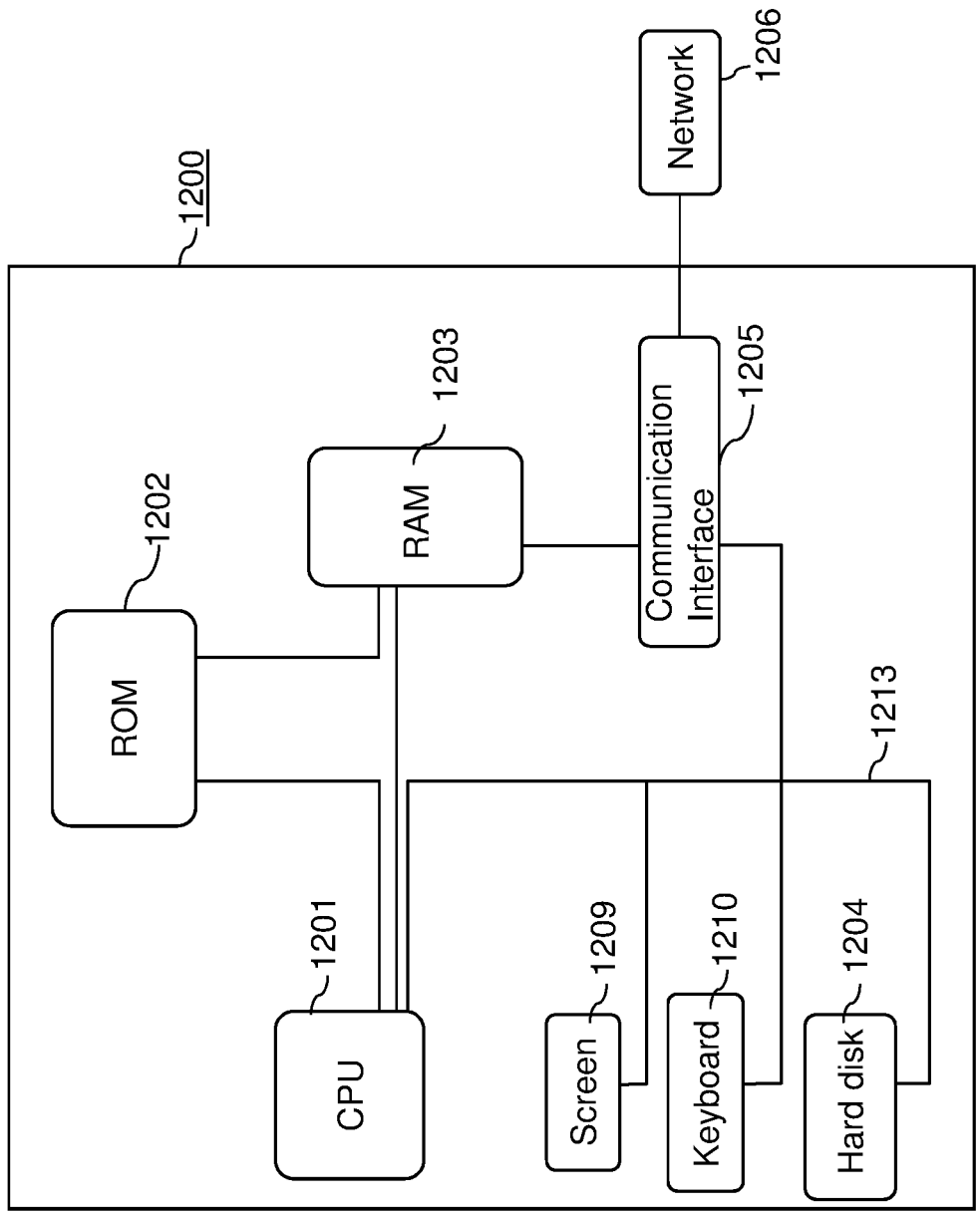
FIG. 12 shows a schematic diagram of an embodiment of a computer that may be used with one or more embodiments of a full-range OCT technique(s) in accordance with one or more aspects of the present disclosure.

Various components of a computer system 1200 are provided in FIG. 12. A computer system 1200 may include a CPU 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 12). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a continuous acquisition system, such as the system 100 discussed herein above, via one or more lines 1213), and one or more other computer systems 1200 may include one or more combinations of the other aforementioned components. The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used to obtain continuous A-lines for OCT imaging. The system 1200 may further include one or more processors connected via a network connection (e.g., via network 1206). The CPU 1201 and any additional processor being used by the system 1200 may be located in the same telecom network or in different telecom networks (e.g., achieving continuous A-lines may be controlled remotely).

The I/O or communication interface 1205 provides communication interfaces to input and output devices, which may include the light source 101, a spectrometer, a microphone, a communication cable and a network (either wired or wireless), a keyboard 1210, a mouse, a touch screen or screen 1209, a light pen and so on. The Monitor interface or screen 1209 provides communication interfaces thereto.

Any methods and/or data of the present disclosure, such as the methods for achieving continuous A-lines as discussed herein, may be stored on a computer-readable storage medium. A computer-readable and/or writable storage medium used commonly, such as, but not limited to, a hard disk (e.g., the hard disk 1204, a magnetic disk, etc.), a flash memory, a CD, an optical disc (e.g., a DVD, Blu-ray, etc.), a magneto-optical disk, a RAM (such as the RAM 1203), a DRAM or the like (e.g., other semiconductor memory, such as, but not limited to, a non-volatile memory card, a solid state drive, SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc.

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 12. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 12) may also include and/or be made of one or more microprocessors and/or nanoprocessors. Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution.

The present disclosure and/or one or more components of devices, systems and storage mediums, and/or methods, thereof also may be used in conjunction with any suitable optical assembly including, but not limited to, arrangements and methods for providing multimodality microscopic imaging of one or more biological structure, such as those disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942 and U.S. Patent Publication Nos. 2010/0092389, 2012/0101374 and 2016/0228097, each of which patents and patent publications are incorporated by reference herein in their entireties.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure.

The invention claimed is:

1. A continuously full-range optical coherence tomography system for continuously acquiring A-line data, the system comprising:
   a light source that operates to produce a light;
   an interference optical system that operates to: (i) receive and divide the light from the light source into a first light with which an object or sample is to be irradiated and a second reference light, (ii) send the second reference light for reflection off of a reference mirror of the interference optical system, and (iii) generate interference light by causing reflected or scattered light of the first light with which the object or sample has been irradiated and the reflected second reference light to combine or recombine, and to interfere, with each other, the interference light generating one or more interference patterns; and
   a detector that operates to continuously acquire the interference light and/or the one or more interference patterns such that continuous A-lines are obtained continuously from frame to frame so that the A-lines are obtained immediately in succession and to measure the interference or the one or more interference patterns between the combined or recombined light.

2. The continuously full-range optical coherence tomography system of claim 1, wherein the detector obtains continuous A-lines such that continuous images of the object or sample are obtained without losing one or more A-lines, from frame to frame, and/or without occurring artifacts during signal processing.

3. The continuously full-range optical coherence tomography system of claim 1, wherein one or more of the following occurs:
   (i) the interference optical system further includes a phase shift device that operates to apply phase modulation to a light passing through the phase shift device and/or the interference optical system;
   (ii) the phase modulation is applied with positive and negative constant frequency;
   (iii) the absolute value of the frequency is approximately a quarter of an A-line rate, which is the rate to acquire an axial OCT profile; and
   (iv) the phase shift device sinusoidally modulates the interference or the interference patterns.

4. The continuously full-range optical coherence tomography system of claim 1, wherein the interference optical system further includes a phase shift device that operates to apply phase modulation to a light passing through the phase shift device and/or the interference optical system, the phase shift device including a fiber, a collimator lens, a galvanometer scanner having a scanning mirror, and a focusing lens, wherein the fiber sends the light passing through the phase shift device and/or the interference optical system through the collimator lens to produce a collimated light beam from the collimator lens, the collimated light beam is reflected at an offset from a pivot point of the galvanometer scanner to and through the focusing lens to reflect off of the reference mirror or off of the object or sample and be transmitted back through the focusing lens, off of the galvanometer scanner, through the collimator lens, and back into the fiber.

5. The continuously full-range optical coherence tomography system of claim 4, wherein the galvanometer scanner is applied with or to a voltage with a triangle shape, the voltage having continuity or absolute constant frequency to one or more of: (i) obtain continuous images without losing any A-lines from frame to frame, (ii) avoid lost or dead A-lines from occurring during setting up positioning from frame to frame, and (iii) modulate the optical path length linearly with time.

6. The continuously full-range optical coherence tomography system of claim 4, wherein:
   (i) the phase shift device is disposed in a reference arm of the interference optical system;
   (ii) the reference mirror further operates to reflect the second reference light back through the phase shift device; and
   (iii) the phase shift device operates to apply the phase modulation to or in the reference light passing through the phase shift device and/or the interference optical system.

7. The continuously full-range optical coherence tomography system of claim 5, further comprising:
   (i) a first circulator;
   (ii) a second circulator;
   (iii) a patient interface device;
   (iv) a common path probe that: (a) receives light from the light source via the first circulator, the optical interference system, and the patient interface device, and (b) sends both the first light and the second reference light, which pass through the common path probe to reduce and/or cancel one or more phase noises, back to the optical interference system through the patient interface device such that the optical interference system splits the first light to go to the first circulator and splits the second reference light to go to the second circulator;
   (v) a length adjustment section disposed in the reference arm; and
   (vi) a combiner that operates to: (a) receive the first light via the first circulator, (b) receive the reflected second reference light, after being sent through the phase shift device via the length adjustment section, and (c) combine the first light and the reflected second reference light for delivery to the detector.

8. The continuously full-range optical coherence tomography system of claim 4, wherein:
   (i) the phase shift device is disposed in a sample arm of the optical interference system;

(ii) the light passing through the phase shift device and/or the optical interference system is the first light;
(iii) the object or sample reflects the first light through the focusing lens of the phase shift device; and
(iv) the phase shift device operates to apply the phase modulation to or in the first light passing through the phase shift device and/or the optical interference system.

9. The continuously full-range optical coherence tomography system of claim 4, wherein an optical path length during scanning changes because the collimated light is reflected at the offset from the pivot point of the galvanometer scanner.

10. The continuously full-range optical coherence tomography system of claim 1, further comprising a patient interface device and a catheter disposed in a sample arm of the interference optical system such that: (i) the first light passes through the patient interface device and the catheter to irradiate the object or the sample, and (ii) the reflected or scattered light of the first light with which the object or sample has been irradiated passes through the catheter and the patient interface device to be combined or recombined, and to interfere, with the reflected second reference light.

11. The continuously full-range optical coherence tomography system of claim 1, further comprising:
(i) a first circulator;
(ii) a length adjustment section disposed in a reference arm that receives the second reference light from the optical interference system so that the second reference light reflects off of the reference mirror, via the length adjustment section; and
(iii) a combiner that operates to: (a) receive the first light and the reflected second reference light via the first circulator and the optical interference system, and (b) combine the first light and the reflected second reference light for delivery to the detector.

12. The continuously full-range optical coherence tomography system of claim 1, wherein the interference optical system includes one or more of: an interferometer and a beam splitter that operates to perform the division of the light from the light source into the first light and the second reference light,
wherein the interferometer and/or the beam splitter cause the first light to pass into a sample arm of the interference optical system and cause the second reference light to pass into a reference arm of the interference optical system, and
wherein the beam splitter or a light splitting component of the interferometer are positioned or disposed at an angle to the reference mirror, the detector, and the object or sample.

13. A method for performing continuous full-range optical coherence tomography ("OCT") using a continuous full-range OCT device or system having a light source, an interference optical system that operates to generate interference light and one or more interference patterns from a light from the light source that has been split into a first light with which an object or sample has been irradiated and a second reference light, and a detector, the method comprising:
continuously acquiring, via the detector, the interference light and/or the one or more interference patterns such that continuous A-lines are obtained continuously from frame to frame so that the A-lines are obtained immediately in succession; and
measuring the interference or the one or more interference patterns.

14. The method of claim 13, wherein the detector obtains continuous A-lines such that continuous images of the object or sample are obtained, from frame to frame, without losing one or more A-lines and/or without occurring artifacts during signal processing.

15. The method of claim 13, further comprising applying phase modulation to a light passing through a phase shift device of the OCT device or system, wherein the phase shift device includes a fiber, a collimator lens, a galvanometer scanner having a scanning mirror, and a focusing lens, and
wherein the fiber sends the light passing through the fiber through the collimator lens to produce a collimated light beam from the collimator lens, the collimated light beam is reflected at an offset from a pivot point of the galvanometer scanner to and through the focusing lens to reflect off of a reference mirror or off of the object or sample and be transmitted back through the focusing lens, off of the galvanometer scanner, through the collimator lens, and back into the fiber.

16. A method for processing at least one interference or interference pattern signal generated from a continuous full-range optical coherence tomography ("OCT") device or system having a light source, an interference optical system that operates to generate interference light and one or more interference patterns from a light from the light source that has been split into a first light with which an object or sample has been irradiated and a second reference light, and a detector, the method comprising:
continuously acquiring, via the detector of the OCT device or system, the interference light and/or the one or more interference patterns to generate the interference or interference pattern signal and such that continuous A-lines are obtained continuously from frame to frame so that the A-lines are obtained immediately in succession.

17. The method of claim 16, wherein the continuous acquisition step further comprises acquiring a 2D array of data and 2D background data, wherein the 2D background data is obtained without data from the first light with which an object or sample has been irradiated.

18. The method of claim 17, further comprising performing background subtraction or time average 2D background subtraction on the 2D array of data by having the detected 2D array be subtracted with the 2D background data to reduce or minimize any DC noise and fixed pattern noises.

19. The method of claim 17, further comprising remapping the data to k-space.

20. The method of claim 16, further comprising performing DC and fixed pattern noise reduction using a noise reduction algorism.

21. The method of claim 16, further comprising performing dispersion compensation or correction after one or more of: (i) performing background subtraction or time average 2D background subtraction on a 2D array of data by having a detected 2D array be subtracted with 2D background data to reduce or minimize any DC noise and fixed pattern noises; (ii) performing DC and fixed pattern noise reduction using a noise reduction algorism; and (iii) applying a shifted Heaviside step Window function to have either a positive or negative modulated peak along, to, or with the B-scan direction.

22. The method of claim 16, further comprising shifting or rotating OCT images by a phase delay, modulated by a phase shift device, of each A-line of each of frames to compensate a different phase delay applied to each A-line.

23. The continuously full-range optical coherence tomography system of claim 1, wherein one or more of the following occur:
  (i) the continuously full-range optical coherence tomography system further comprises additional detectors that operate to, along with the detector, continuously acquire the interference light and/or the one or more interference patterns such that continuous A-lines are obtained continuously from frame to frame so that the A-lines are obtained immediately in succession and to measure the interference or the one or more interference patterns between the combined or recombined light;
  (ii) the entire reflected second reference light combines or recombines, and interferes, with the entire first light to generate the interference light and/or the one or more interference patterns; and
  (iii) the continuous acquisition of the A-lines, from frame to frame, avoids discontinuity or delay between frames and scans of the A-lines.

* * * * *